United States Patent
Schümann et al.

(10) Patent No.: US 7,481,097 B2
(45) Date of Patent: Jan. 27, 2009

(54) METHOD AND DEVICE FOR MEASURING THE SURFACE TENSION OF LIQUIDS

(75) Inventors: Daniel Schümann, Dresden (DE); Rainer Münzner, Schwarzenberg (DE)

(73) Assignee: E.G.O. Elektro-Geraetebau GmbH, Oberderdingen (DE)

( * ) Notice: Subject to any disclaimer, the term of this patent is extended or adjusted under 35 U.S.C. 154(b) by 0 days.

(21) Appl. No.: 11/839,634

(22) Filed: Aug. 16, 2007

(65) Prior Publication Data

US 2007/0277597 A1 Dec. 6, 2007

Related U.S. Application Data

(63) Continuation of application No. PCT/EP2006/001537, filed on Feb. 21, 2006.

(30) Foreign Application Priority Data

Feb. 21, 2005 (DE) ........................ 10 2005 007 870

(51) Int. Cl.
*G01N 13/00* (2006.01)
(52) U.S. Cl. ..................................... 73/64.51
(58) Field of Classification Search ................ 73/64.48, 73/64.51
See application file for complete search history.

(56) References Cited

U.S. PATENT DOCUMENTS

| | | | | |
|---|---|---|---|---|
| 2,401,053 A | * | 5/1946 | Cupples | 73/64.51 |
| 3,881,344 A | * | 5/1975 | Jobe | 73/64.51 |
| 4,410,329 A | | 10/1983 | Blevins et al. | |
| 4,416,148 A | * | 11/1983 | Klus et al. | 73/64.51 |
| 4,527,421 A | * | 7/1985 | Miller, Jr. | 73/64.51 |
| 5,661,234 A | * | 8/1997 | Gerits et al. | 73/64.48 |
| 6,085,577 A | * | 7/2000 | Christensen et al. | 73/64.51 |

(Continued)

FOREIGN PATENT DOCUMENTS

DE 197 55 291 5/1999

(Continued)

OTHER PUBLICATIONS

Fainerman et al., Accurate Analysis of the Bubble Formation Process in Maximum Bubble Pressure Tensionmetry, Jan. 2004, vol. 75, No. 1, pp. 213-221, Review of Scientific Instruments.

(Continued)

*Primary Examiner*—Hezron Williams
*Assistant Examiner*—John Fitzgerald
(74) *Attorney, Agent, or Firm*—Alston & Bird LLP (57) ABSTRACT

A method and device for measuring the surface tension of liquids uses the bubble pressure principle, wherein a parameter relating to a bubble formed using a defined gas mass flow rate or volume flow rate is measured at the tip of a capillary tube immersed in the liquid. The surface tension is calculated from the measured value. With a defined gas mass flow rate or volume flow rate, the time between the minimum pressure and the maximum pressure and hence a defined pressure increase in a bubble are measured, and from this the surface tension is calculated. A relatively inexpensive sensor for measuring the surface tension in an appliance, such as a washing machine, using this inventive concepts is disclosed using a piezoelectric transducer.

15 Claims, 5 Drawing Sheets

U.S. PATENT DOCUMENTS

| | | |
|---|---|---|
| 6,185,989 B1 | 2/2001 | Schulze |
| 6,915,680 B2 * | 7/2005 | Bicker et al. ............... 73/64.48 |
| 6,932,097 B2 * | 8/2005 | Ellson et al. ................. 137/2 |

FOREIGN PATENT DOCUMENTS

| | | |
|---|---|---|
| DE | 199 33 631 A1 | 2/2001 |
| DE | 20318463 | 3/2004 |
| DE | 20 2004 007 261 | 9/2004 |
| DE | 20 2004 012 573 | 12/2004 |
| EP | 0760472 | 3/1997 |
| EP | 1 464 948 | 10/2004 |
| WO | WO 9417954 | 8/1994 |

OTHER PUBLICATIONS

German Search Report for German Application No. 10 2005 007 870.2.

International Search Report from PCT/EP2006/001537, dated May 26, 2006.

\* cited by examiner

METHOD AND DEVICE FOR MEASURING THE SURFACE TENSION OF LIQUIDS

CROSS REFERENCE TO RELATED APPLICATIONS

This application is a continuation of PCT/EP2006/001537, filed Feb. 21, 2006, which is based on German Application No. 10 2005 007 870.2, filed Feb. 21, 2005, of which the contents of both are hereby incorporated by reference.

FIELD OF INVENTION

The invention generally relates to a method and a device for measuring the surface tension of liquids using the bubble pressure principle, where for a clearly defined gas mass or volume flow, a bubble parameter is determined on a capillary tube tip immersed in the liquid and the surface tension is calculated therefrom.

BACKGROUND OF INVENTION

The surface tension σ indicates what work has to be effected in order to increase by a specific amount a surface at the liquid-gas interface. It therefore gives information e.g., on the concentration and effectiveness of surfactants in liquids, e.g. for the quality control of inks or waters in washing and cleaning processes.

With the bubble pressure principle a gas or gas mixture, usually air, is forced through a capillary tube connected to a pneumatic system into a liquid to be analyzed and the internal pressure p of the bubble forming on the capillary tube is measured.

In the maximum bubble pressure method the maximum bubble pressure $p_{max}$ is measured. The hydrostatic pressure $p_h$ acting on the bubble is calculated from the immersion depth $h_E$ of the capillary tube, which has to be detected and adjusted in a complicated manner, and the liquid density. The surface tension σ is then calculated with the radius of the capillary $r_{cap}$ in a first approximation according to:

$$\sigma = r_{cap}/2(p_{max} - p_h) \quad (1)$$

In a differential pressure method on a capillary tube derived from this (DE 197 55 291 C1, DE 203 18 463 U1) the dynamic surface tension σ is calculated using the correlation K between the surface tension σ and the differential pressure Δp between the maximum internal pressure $p_{max}$ and the minimum internal pressure $p_{min}$ of the bubble:

$$\sigma = K \cdot \Delta p \text{ with } \Delta p = p_{max} - p_{min} \quad (2)$$

On the basis of the same action of the hydrostatic pressure on $p_{min}$ and $p_{max}$, unlike in the maximum bubble pressure method, the measurement remains independent of the capillary tube immersion depth.

In surfactant-containing liquids the measured value of the surface tension σ is dependent on the age of the expanding surface, because with increasing bubble life surfactants can be increasingly attached to a newly formed bubble surface. Thus, the bubble pressure principle consequently determines a dynamic surface tension, so that a measured value must always be given in connection with the associated bubble formation time or bubble life $t_{life}$, this being understood to mean hereinafter the time between the pressure minimum and pressure maximum of the bubble.

Known bubble pressure methods measure at a clearly defined bubble frequency or bubble life of the exiting gas bubbles, which must be constantly readjusted in accordance with the dynamically changing surface tension (DE 197 55 291 C1), the maximum bubble pressure or the differential pressure at a capillary tube. A controllable air pump or an air flow-controlling valve is required for this.

To be able to sufficiently accurately measure the surface tension, the pressure sensor used must have a high measuring accuracy compared with other applications.

Pressure sensors meeting these demands must be temperature-compensated and calibrated and therefore constitute the most costly component of a measuring system.

Alternatives to the transformation of the bubble pressure into an electrical signal are sound pressure transducers such as condenser, moving coil, crystal and carbon microphones as well as piezoelectric disks (EP 760 472 B1, EP 902 887 A1). Thus, according to EP 760 472 B1 using a cost effective sound pressure transducer the first derivation of the pressure signal after time is measured and by subsequent integration the bubble pressure and from this the surface tension is determined. It is impossible to avoid measurement errors resulting from the influence of the ambient temperature, atmospheric humidity, frequency dependence of the microphones in the transmission behaviour and drift during a measurement. Sound pressure transducers do not meet the accuracy requirements in connection with a pressure measurement without taking additional measures.

It is known from EP 682 588 A1, that in the case of adequately constant air flows the measured bubble frequency of the bubbles forming on a capillary tube is correlated with the surface tension. With decreasing surface tension the bubble frequency rises. The reciprocal of the bubble frequency, the bubble period time, is formed from the bubble life and the so-called bubble dead time (DE 203 18 463 U1). The bubble dead time designates the time between the pressure maximum following the passage of which the bubble collapses and is inflated and bubble detachment. Even minor flow patterns in the liquid or mechanical vibrations influence the bubble detachment in a random manner and consequently lead to high measurement errors on measuring the surface tension through the bubble frequency. The resulting measurement accuracy is not adequate e.g. for the determination of the detergent concentration in the textile cleaning sector.

Hitherto in the textile and dishwashing sector, particularly in the domestic field, no economic, marketable solution is known with which the surface tension can be sufficiently precisely measured for concentration determination of the detergent or washing agent and on the basis of this an automatic dosing or metering.

BRIEF DESCRIPTION OF THE DRAWINGS

The invention is explained in greater detail relative to an embodiment and the attached drawings, wherein show.

DETAILED DESCRIPTION

On the basis of the dependence of the bubble life on the surface tension with a clearly defined gas mass or gas volume flow, one problem addressed by the invention is to give a method and device for the dynamic measurement of the surface tension of a liquid, which with comparatively limited sensor expenditure provides sufficiently accurate measurement results for most applications.

According to one embodiment of the invention the problem is solved with the features given in claims 1. Advantageous further developments are provided in the other claims.

The method according to the invention is based on the dependence of the bubble life $t_{life}$ on the surface tension in the case of a clearly defined gas mass or volume flow introduced into a system volume.

When a bubble is formed at the end of the capillary tube, the differential pressure between pressure minimum and pressure maximum in the bubble is correlated with the surface tension σ, such as when introducing a clearly defined gas mass or volume flow, usually an air mass or volume flow, into the pneumatic system volume, independently of the surface tension σ, during the same time period the same gas mass or volume always flows into the same. Therefore the bubble life is also dependent on the surface tension σ, because with a lower surface tension σ a lower pressure is built up in the bubble and consequently up to the reaching of the maximum pressure, less gas has to be compressed in the system volume. Therefore the point in time of the pressure maximum is more rapidly reached with a lower surface tension than with a high surface tension. The novel method, referred to as the bubble life method, at a clearly defined gas mass or volume flow measures the bubble life of a bubble forced into the liquid and from this calculates the liquid surface tension.

The precision requirements on a pressure to voltage signal converter are low compared with the known differential pressure measurement method, because it is only necessary to adequately precisely determine the point in time of the pressure minimum and the point in time of the following pressure maximum of a bubble from the pressure signal. The pressure to voltage signal converter does not have to be temperature-compensated or calibrated with respect to the signal amplitude and shift.

In place of pressure sensors it is advantageously possible to use simple and therefore inexpensive sound pressure transducers, e.g. piezoelectric disks. In the case of the direct piezo-electric effect, mechanical deformations caused by pressure changes lead to a mutual shift of the charge mass centres of the crystal atoms. Within the crystal there is an electrical polarization P and surface charges to the outside can be measured. As proportionality exists between the magnitude of the mechanical stress of the piezoelectric crystal and the surface charge quantity, the time points (e.g., points in time) of pressure minimum and pressure maximum can be readily detected as electrical signals. Simple piezoelectric sound transducers are mass produced for the reversed use in piezo-electric buzzers and are extremely inexpensive.

Figure 1:
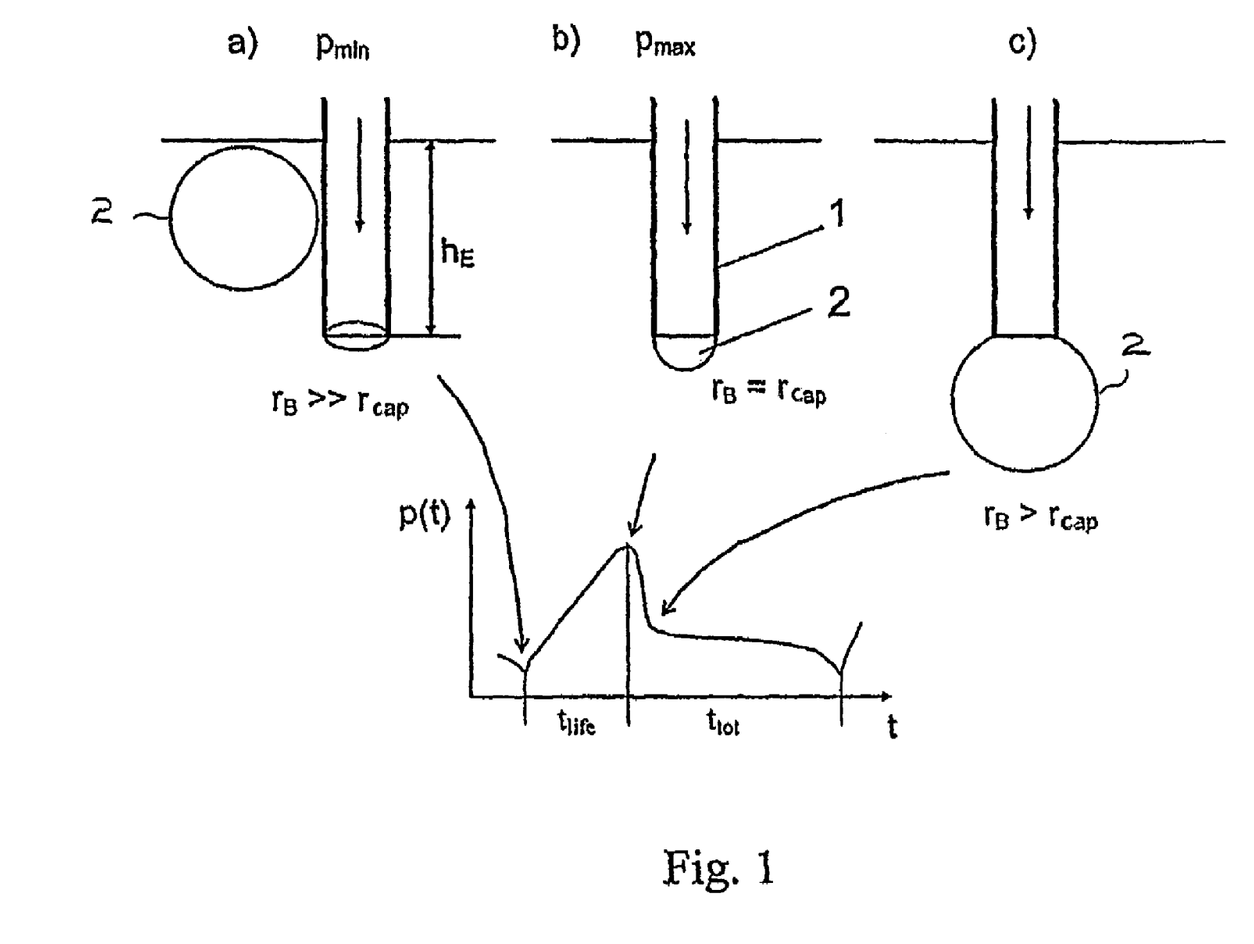
FIG. 1 illustrates the bubble formation and the path of the bubble internal pressure based on a bubble pressure method.
Figure 2:
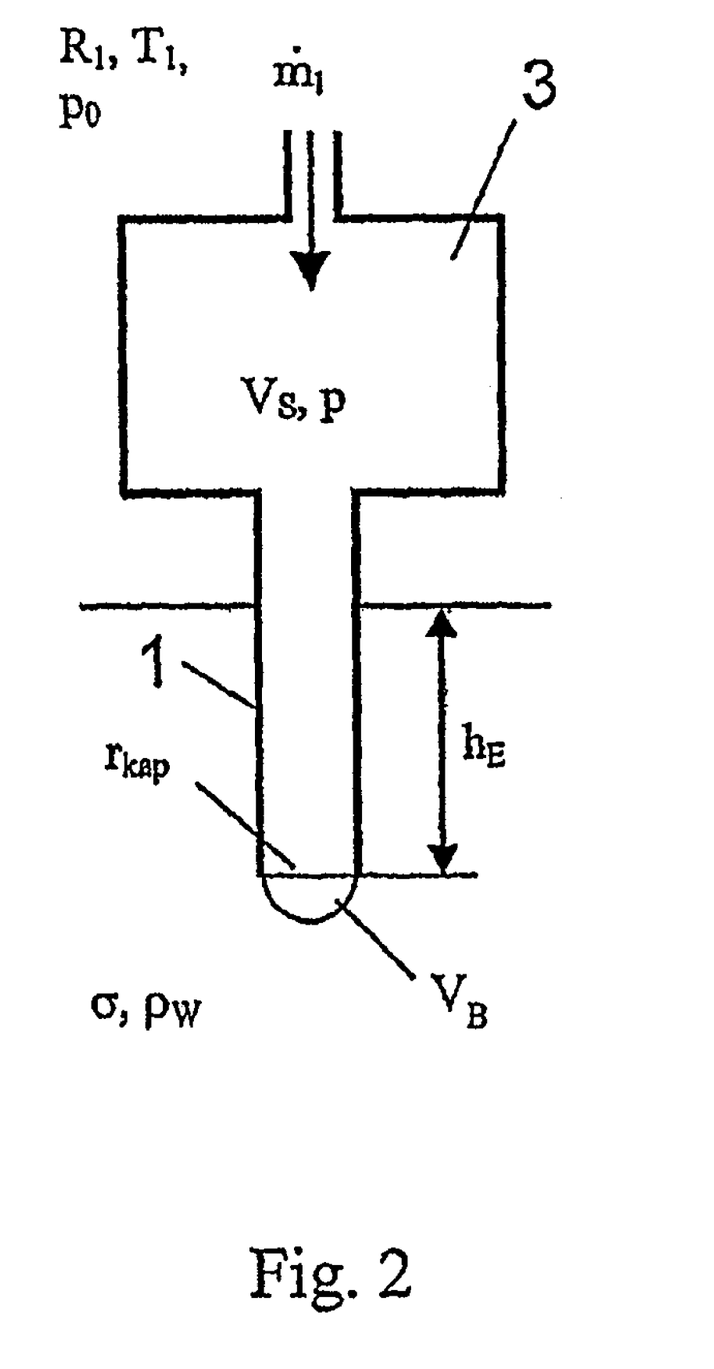
FIG. 2 illustrates a pneumatic system for illustrating the physical bases of the invention.

As is diagrammatically shown in FIG. 1, in the case of a bubble pressure method for measuring the surface tension, air or some other suitable gas or gas mixture is forced through a capillary tube 1 into the liquid to be analyzed. A pressure-voltage converter illustrated in greater detail in FIG. 5 detects the internal pressure p of a bubble 2 forming at the tip of a capillary tube 1. As is apparent from FIG. 1a, a new bubble 2 has a large radius $r_B \gg r_{cap}$ and the pneumatic system connected to the capillary 1 and illustrated in greater detail in FIG. 2, is under the lowest pressure $p_{min}$. As a result of the afterflowing air, the pressure p in bubble 2 (in FIG. 1b) rises. Bubble 2 bulges at capillary tube 1 (FIG. 1b) and the radius of the bubble $r_B$ decreases. If the bubble 2 reaches its minimum radius, which is approximately the same as the capillary tube radius $r_B = r_{cap}$, the pressure in the interior rises to the pressure maximum $p_{max}$ (see, e.g., FIG. 1b). The time from the start of the formation of a bubble 2 up to the reaching of the pressure maximum $p_{max}$ gives the surface age or bubble life $t_{life}$ of a bubble. After exceeding the pressure maximum $p_{max}$ the bubble 2 bursts: $r_B > r_{cap}$ and the pressure p in the interior of bubble 2 rapidly drops through the volume expansion (FIG. 1c). Then the air flow slowly inflates the bubble 2 again until it tilts upwards and is detached from the capillary tube 1 (see, e.g., FIG. 1a). The time period from the pressure maximum $p_{max}$ to the detachment of the bubble 2 is called the dead time $t_{dead}$. Then the process is repeated through the formation of the next bubble. The number of bubbles 2 formed per time unit is called the bubble frequency $f_B$.

On introducing a clearly defined gas mass or volume flow into the pneumatic system volume, the bubble life $t_{life}$ decreases more strongly than the bubble dead time $t_{dead}$ with falling surface tension σ. Thus, with the bubble life it is possible to better resolve a surface tension change than with using the bubble dead time. Even minor variation in the flows in the liquid to be measured, together with mechanical vibrations, influence bubble detachment in a random manner, and therefore the bubble dead time and also the bubble frequency. It is clear that the bubble frequency is unsuitable for determining the surface tension.

According to one embodiment of the present invention, the bubble life $t_{life}$ of a bubble is measured in such a way that it permits the attainment of adequately precise results using extremely inexpensive sensors.

The basic principles of the method will be explained relative to FIGS. 2 and 3. FIG. 2 diagrammatically shows the pneumatic system for a bubble pressure method with the system volume $V_S$, in which is enclosed the volume of capillary tube 1, bubble pressure p, bubble volume $V_B$ and an air mass flow m'1. For the subsequent calculation, a constant air mass flow m'1 and a constant air temperature $T_1$ is assumed, as is air as the ideal gas and a pressure minimum $p_{min}$ equal to the hydrostatic pressure $p_h$.

The starting point for the analysis of the pneumatic system is the thermal equation of state of an ideal gas:

$$p V = m R_G T \tag{3}$$

Into the system volume 3 flows a constant air mass flow m'1. In the time $t_{life}$ the pressure rises from $p_h$ to $p_{max} = f(\sigma)$. The total volume $V_G$ rises from $V_s$ to $V_s + V_B$.

The air mass which has been received during the time $t_{life}$ is calculated as follows:

$$m = m' \cdot t_{life} \tag{4}$$

On the basis of the observations, equation (3) for the time point of maximum bubble pressure can be written as follows:

$$(\Delta p + p_h)(V_S + \Delta V) = (m_0 + \Delta m) R_{air} T_{air} \tag{5}$$

$$(p_{max} - p_h + p_h)(V_S + V_B) = (m_0 + m' \cdot t_{life}) R_{air} T_{air} \tag{6}$$

$m_0$ is calculated using equation (3) to give $$m_0 = (p_h \cdot V_S)/(R_{air} \cdot T_{air}) \tag{7}$$

equation (7), inserted in (6), gives:

$$p_{max}(V_S+V_B)=((p_h \cdot V_S)/(R_{air} \cdot T_{air})+m' \cdot t_{life})R_{air}T_{air} \qquad (8)$$

transposed according to $t_{life}$, it follows:

$$t_{life}=(p_{max}(V_S+V_B)-p_h \cdot V_S)/m' \cdot R_{air}T_{air} \qquad (9)$$

with the hydrostatic pressure $$p_h=\rho_w \cdot g \cdot h_E p_0 \qquad (10)$$

and the maximum pressure as a function of the surface tension (first approximation):

$$p\text{max}=(2\sigma/r_{cap})+p_h \qquad (11)$$

and the bubble volume at maximum bubble pressure:

$$V_B=2/3\pi \cdot r_{cap}^3 \qquad (12)$$

through insertion in equation (9), it is obtained:

$$t_{life}=((2\sigma/r_{cap}+\rho_w g\, h_e+p_0)(V_S+2/3\pi \cdot r_{cap}^3)-(\rho_w g\, h_E+p_0)\cdot V_S)/m' \cdot R_{air}T_{air} \qquad (13)$$

By transposing equation (13), it is obtained:

$$t_{life}=(2\sigma/r_{cap}(V_S+2/3\pi \cdot r_{cap}^3)+(\rho_w g\, h_E+p_0)\cdot 2/3\pi \cdot r_{cap}^3)/m' \cdot R_{air}T_{air} \qquad (14)$$

On the basis of equation (14) it can be seen that the bubble life $t_{life}$ in the case of a constant air mass flow is linearly dependent on the surface tension $\sigma$ of a liquid:

$$t_{life}=f(\sigma),\; m'_{air}=\text{const} \qquad (15)$$

Figure 3:
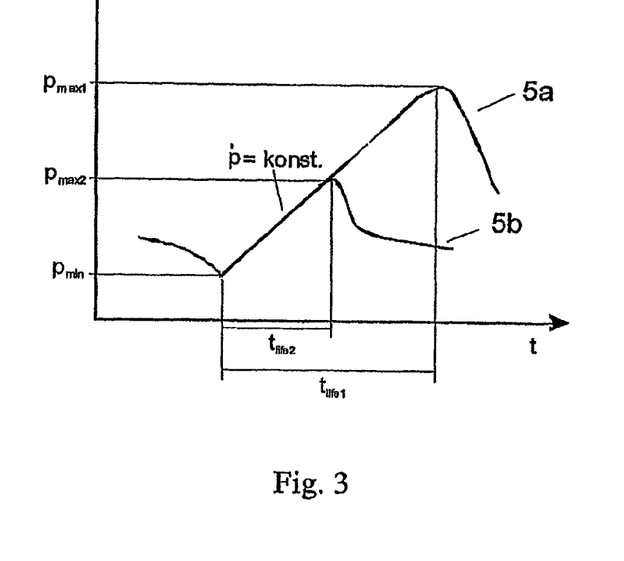
FIG. 3 illustrates a graphical representation of bubble pressure signals of different surface tensions for a constant air mass flow.

FIG. 3 shows the pressure gradient of a bubble at different surface tensions and unlike the normal procedure, the bubble life $t_{life}$ is not kept constant and instead through the constantly introduced air mass flow $m'_1$ the pressure rise in the bubble from pressure minimum $p_{min}$ to pressure maximum $p_{max1}$ or $p_{max2}$; dp/dt=const. According to the invention, the bubble life $t_{life}$ of a bubble is measured instead of the pressure difference $\Delta p=p_{max}-p_{min}$ in a bubble. As is shown in FIG. 3, the internal pressure 5b of a bubble in a liquid with a lower surface tension $\sigma_2$ reaches the pressure maximum $p_{max2}$ with a shorter bubble life $t_{life2}$ compared with the internal pressure 5a of a bubble in a liquid with a higher surface tension $\sigma_1$, which only reaches the pressure maximum $p_{max1}$ after a longer bubble life $t_{life1}$.

Figure 4:
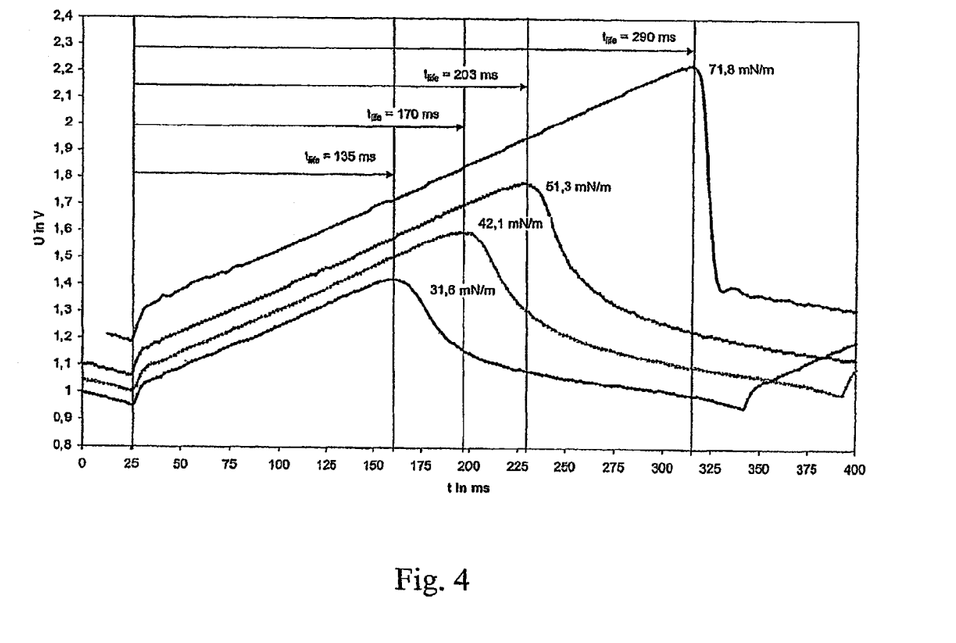
FIG. 4 illustrates measurement results for different liquids.

FIG. 4 is a graph with bubble pressure signals of liquids with different surface tension and a constant air mass flow. All the bubble pressure signals rise in the same way up to a maximum bubble pressure dependent on the surface tension. For the lower surface tension bubble pressure signals, the pressure minimum is lower, because following bubble detachment there is an initial covering of the surface with surfactants and consequently there is a lower surface tension at the pressure minimum.

The resolution of the surface tension by measuring the bubble life is dependent on the reference bubble life, which is set, e.g., by the air mass flow in water. In the case of a reference bubble life of 300 ms set in water (cf. FIG. 4), there is already a sensitivity of 3.9 ms per 1 mN/m. A calibration of the surface tension sensor can take place in water with known temperature and consequently known surface tension, in that the bubble life is measured and is used as the reference bubble life. With this procedure it is advantageously possible to obviate the need for regulating the gas mass or volume flow.

Figure 5:
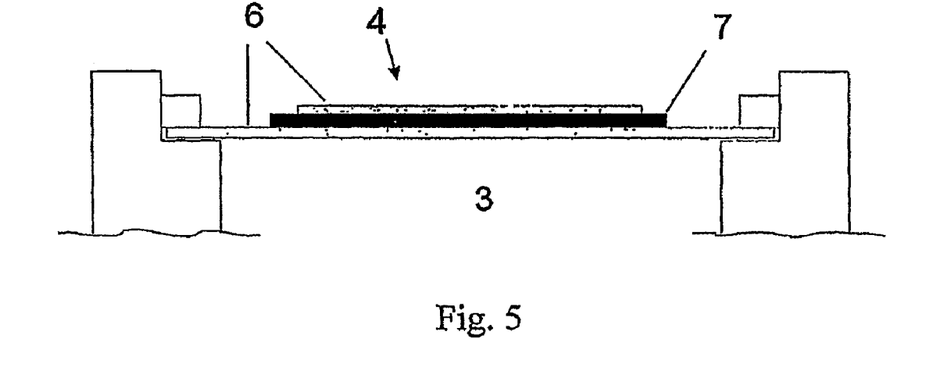
FIG. 5 illustrates a diagrammatically represented piezo-electric sound pressure transducer.

FIG. 5 shows the use of a piezoelectric transducer as a sound pressure transducer for the aforementioned method. A piezoelectric sound pressure transducer 4 is connected to an appropriate point of the system volume 3. The piezoelectric sound pressure transducer 4 comprises two metallic contact surfaces 6 with leads, between which is bonded a so-called piezoelectric crystal 7. When there is a pressure change in pneumatic system 3, the piezoelectric sound pressure transducer 4 produces a charge shift at the contact surfaces 6. The time change to the pressure or the derivation of the bubble pressure after time dp/dt is proportional to the externally measured current. By integrating the measured current by means of an evaluating circuit it is possible to generate a voltage signal u(t), which is proportional to the pressure signal. Since, according to the invention, only the time period $t_{life}$ between pressure minimum $p_{min}$ and pressure maximum $p_{max}$ are of interest, whereas no interest is attached to the level of the maximum pressure or maximum differential pressure, there are significant cost reductions with respect to an evaluating circuit. The $t_{life}$ can be determined using, for example, an inexpensive microcontroller.

Figure 6:
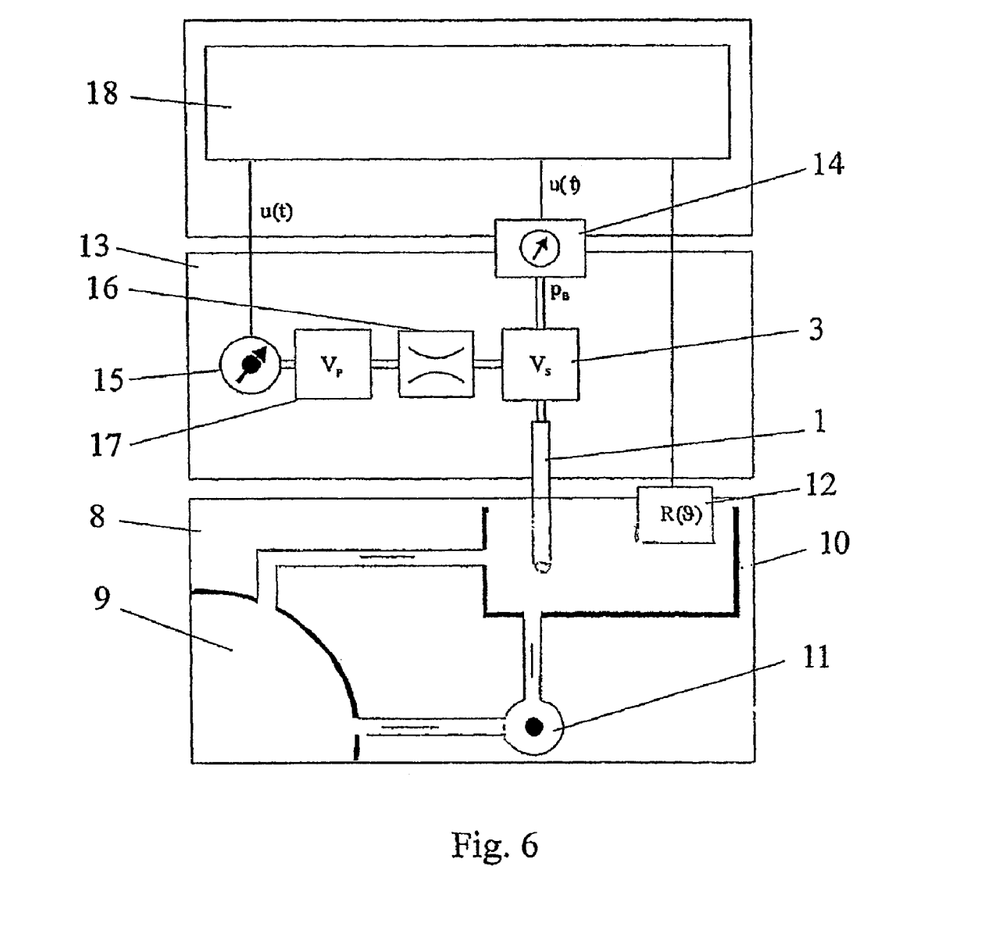
FIG. 6 illustrates one embodiment of a function structure for the surface tension measurement in a washing machine.

FIG. 6 shows a function structure for an application in an appliance, such as a washing machine, using the inventive bubble life method.

In the fluidic part 8 of the washing machine, in the bypass to a detergent solution container 9, is provided a measuring vessel 10, to which is supplied by a detergent solution pump 11 process-controlled detergent solution and thorough mixing takes place there. As the surface tension of a liquid is very highly temperature-dependent, a temperature sensor 12 measures the detergent solution temperature 9.

The pneumatics 13 comprise capillary tube 1, system volume 3, the pressure sensor or sound pressure transducer 14 and the constant air quantity source 15, 16, 17. In the present embodiment an air pump 15, e.g. a diaphragm pump with motor or piezoelectric drive, by means of a buffer volume 17 forces through a choke 16 air into the pneumatic system and to it are connected on the one hand the pressure sensor or sound pressure transducer 14 and on the other a capillary tube 1. The choke 16 is used for setting the operating point of air pump 15 and prevents as a maximum size pneumatic resistor any effects of the bubble pressure on the operating point thereof. Another possibility is constituted by the connection of a gas pressure container. The tip of capillary tube 1 is immersed in the measurement vessel 10.

Not shown are the electronics that evaluate the signals u(t) taken from the pressure sensor or sound pressure transducer 14, as well as the signals emanating from temperature sensor 12 and controls the measurement process. The electronics interface to the washing machine control components.

The surface tension sensor is calibrated in water of known temperature and therefore known surface tension ($\sigma$), in that, in the above-described manner, the bubble life $t_{life}$ is measured and from it is calculated the gas mass or volume flow (m'1). The measuring or calibrating process starts with the switching on of pump 15 and after a clearly defined time during which an adequately constant pressure has built up in buffer volume 17, the bubble life $t_{life}$ is determined. When using the surface tension sensor in a washing machine, it is calibrated at water intake times, the washing machine drum being stationary during the measurement and calibration processes.

Figure 7:
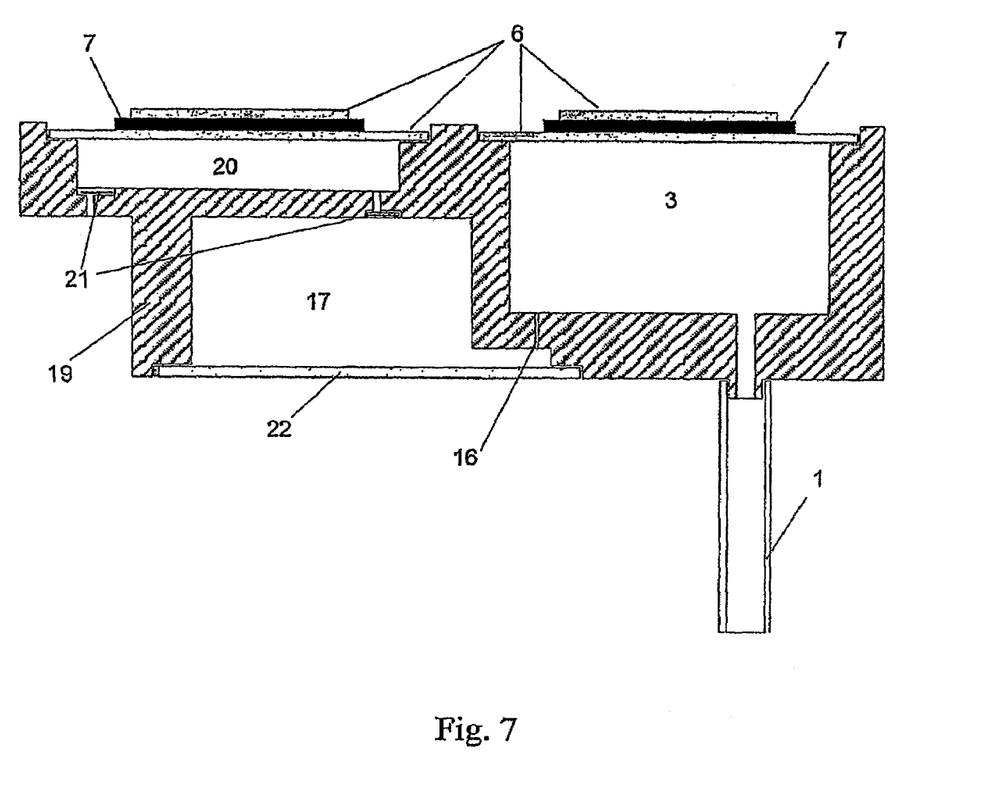
FIG. 7 illustrates a diagrammatic section through a compact surface tension sensor operating according to one embodiment of the invention.

FIG. 7 is a diagrammatic section through a compact surface tension sensor operating according to the inventive method. Into said compact surface tension sensor are integrated an air pump, a buffer volume, a choke, the system volume, the piezoelectric sound pressure transducer and the capillary tube.

The compact surface tension sensor comprises a base member 19 on which are formed a connection for capillary tube 1 and system volume area 3, choke 16, buffer volume area 17, a pump chamber 20 and pump valves with holders for valve flaps 21.

The system volume 3 is closed at one end by the piezoelectric transducer 4 described in greater detail relative to FIG. 5. Buffer volume 17 is sealed by a cover 22. A piezoelectric transducer 4 comprising two metallic contact surfaces 6 with leads between which is bonded a so-called piezoelectric crystal 7, closes the pump chamber 20 and forms the diaphragm drive of air pump 15 of FIG. 6.

Such a surface tension sensor can be extremely inexpensively manufactured by a plastic injection moulding process.

The invention claimed is:

1. A method for measuring a surface tension of liquids wherein in the case of a constant gas volume flow in said liquid a bubble life is determined on a capillary tube tip immersed in said liquid,
   wherein from said bubble life is calculated said surface tension,
   wherein said bubble life is measured between a pressure minimum and a pressure maximum of said bubble is at said constant gas volume flow,
   wherein a defined pressure rise of said bubble is calculated using said bubble life measurement and used to calculate said surface tension of said liquid.

2. The method according to claim 1, wherein said surface tension sensor is calibrated in water having a known temperature and a known surface tension by measuring said bubble life and calculating from said bubble life said constant gas volume flow.

3. The method according to claim 1, wherein when using said surface tension sensor in a washing machine, said surface tension sensor is calibrated during water intake time and wherein during said measurement and calibration processes, said washing machine drum is stationary.

4. The method according to claim 1, wherein a gas pressure container with a downstream choke is used for producing said constant gas volume flow in said liquid in a defined manner.

5. The method according to claim 4, wherein said gas pressure container is refillable.

6. The method according to claim 1, wherein a diaphragm pump with a downstream choke is used for producing said gas mass flow or said gas volume flow in said liquid in a defined manner.

7. The method according to claim 6, wherein a buffer volume for smoothing out said constant gas volume flow is provided between said diaphragm pump and said choke.

8. The method according to claim 7, wherein a measuring or calibrating process starts with the switching on of said diaphragm pump and the bubble life is determined after a defined time in which an adequately constant pressure has built up in said buffer volume.

9. The method according to claim 1, wherein said bubble life is measured with a pressure sensor, which detects and signals when said pressure minimum and said pressure maximum of said bubble are reached.

10. The method according to claim 9, wherein said pressure sensor converts said signals of said pressure minimum and said pressure maximum into voltage signals.

11. The method according to claim 10, wherein said pressure sensor comprises a sound pressure transducer from the following group of a condenser, a moving coil, a crystal microphone, a carbon microphone and a piezoelectric disk.

12. A device for measuring a surface tension of liquids comprising:
   a structure provided with a base member, on which is formed a connection for a capillary tube, a system volume, a choke, a buffer volume, a pump chamber and pump valves with holders for valve flaps;
   said capillary tube;
   a piezoelectric transducer sealing said system volume;
   said valve flaps;
   a cover for closing said buffer volume; and
   a piezoelectric transducer as a drive for an air pump.

13. A device for measuring a surface tension of a liquid, comprising:
   a structure forming therein
      a pump chamber, receiving a gas,
      a buffer volume chamber receiving the gas from the pump chamber,
      a system volume chamber, and
      a choke, said choke allowing passage of the gas from said buffer volume chamber to said system volume chamber;
   a first piezoelectric transducer positioned on said structure over said system volume chamber, said first piezoelectric transducer generating signals used to measure a pressure minimum and a pressure maximum of a bubble;
   a second piezoelectric transducer position on said structure over said pump chamber, said second piezoelectric transducer pumping the gas from said pump chamber into said buffer volume chamber;
   a cover positioned on said structure over said buffer volume chamber;
   a plurality of valve flaps attached to said structure wherein a first valve flap allows passage of said gas into said pump chamber and a second valve flap allows passage of said gas from said pump chamber into said buffer volume chamber; and
   a capillary tube having a first end and a second end, said capillary tube attached to said structure at the first end receiving said gas from said system volume chamber, forming said bubble at the second end wherein said bubble manifest said pressure minimum at a first point in time and said pressure maximum at a second point in time.

14. The device according to claim 13 wherein the gas comprises air.

15. The device according to claim 13 wherein the device is housed in a washing machine.

* * * * *

UNITED STATES PATENT AND TRADEMARK OFFICE
CERTIFICATE OF CORRECTION

PATENT NO.         : 7,481,097 B2
APPLICATION NO.    : 11/839634
DATED              : January 27, 2009
INVENTOR(S)        : Schumann et al.

Page 1 of 1

It is certified that error appears in the above-identified patent and that said Letters Patent is hereby corrected as shown below:

Column 7,

Line 21, cancel "is".

Signed and Sealed this

Twenty-first Day of April, 2009

JOHN DOLL
*Acting Director of the United States Patent and Trademark Office*